United States Patent

Heikkilä et al.

Patent Number: 5,816,706
Date of Patent: Oct. 6, 1998

[54] METHOD AND APPARATUS FOR DETERMINING INTERNAL TEMPERATURE AND COEFFICIENT OF INTERNAL THERMAL CONDUCTIVITY IN A STUCTURE

[75] Inventors: Ilkka Heikkilä ; Seppo Nissilä, both of Oulu, Finland

[73] Assignee: Polar Electro OY, Kempele, Finland

[21] Appl. No.: 716,295

[22] PCT Filed: Mar. 23, 1995

[86] PCT No.: PCT/FI95/00155

§ 371 Date: Sep. 24, 1996

§ 102(e) Date: Sep. 24, 1996

[87] PCT Pub. No.: WO95/25946

PCT Pub. Date: Sep. 28, 1995

[30] Foreign Application Priority Data

Mar. 24, 1994 [FI] Finland ................................. 941383

[51] Int. Cl.⁶ ............................. G01K 1/16; G01K 3/00; G01K 3/14; G01K 7/22

[52] U.S. Cl. .................... 374/134; 374/183; 374/110; 374/112; 374/120

[58] Field of Search ............................ 374/134, 135, 374/110, 112, 120, 183

[56] References Cited

U.S. PATENT DOCUMENTS

| | | | |
|---|---|---|---|
| 3,095,743 | 7/1963 | Teasel et al. | 374/134 |
| 3,232,113 | 2/1966 | Malone | 374/134 |
| 3,417,617 | 12/1968 | Rall | 374/165 |
| 3,776,039 | 12/1973 | Bowen | 374/134 |
| 4,245,500 | 1/1981 | Malang | 374/30 |
| 4,541,728 | 9/1985 | Hauser et al. | 374/30 |
| 4,553,852 | 11/1985 | Derderian et al. | 341/30 |
| 5,249,864 | 10/1993 | Fagan et al. | 371/110 |
| 5,294,200 | 3/1994 | Rall | 374/134 |
| 5,484,206 | 1/1996 | Nouldsworth | 374/134 |

FOREIGN PATENT DOCUMENTS

| | | | |
|---|---|---|---|
| 30 48 361 A1 | 7/1982 | Germany . | |
| 3048361 | 7/1982 | Germany | 374/134 |
| 3527942 | 2/1987 | Germany | 374/134 |
| 0029794 | 3/1980 | Japan | 374/134 |
| 0149025 | 11/1980 | Japan | 374/134 |
| 0055826 | 5/1981 | Japan | 374/134 |
| 0305370 | 6/1971 | U.S.S.R. | 374/134 |
| 1 428 170 | 3/1976 | United Kingdom . | |
| 2 182 152 | 5/1987 | United Kingdom . | |
| WO 93/01478 | 1/1993 | WIPO . | |

Primary Examiner—Diego F. F. Gutierrez
Attorney, Agent, or Firm—Hoffmann & Baron, LLP

[57] ABSTRACT

The invention relates to a method and apparatus for determining the internal temperature and the coefficient of internal thermal conductivity of a structure. In both cases, the surface temperature and ambient temperature of an object are measured from both sides of two structures whose thermal conductivities are known. On the basis of the measured temperature values, the internal temperature or the coefficient of internal thermal conductivity of the object is determined from the function of the heat flux. Thereafter the unknown thermal conductivity or the unknown internal temperature of the object is eliminated from the solutions, and the internal temperature or the coefficient of internal thermal conductivity of the object is determined on the basis of the combined solution.

12 Claims, 2 Drawing Sheets

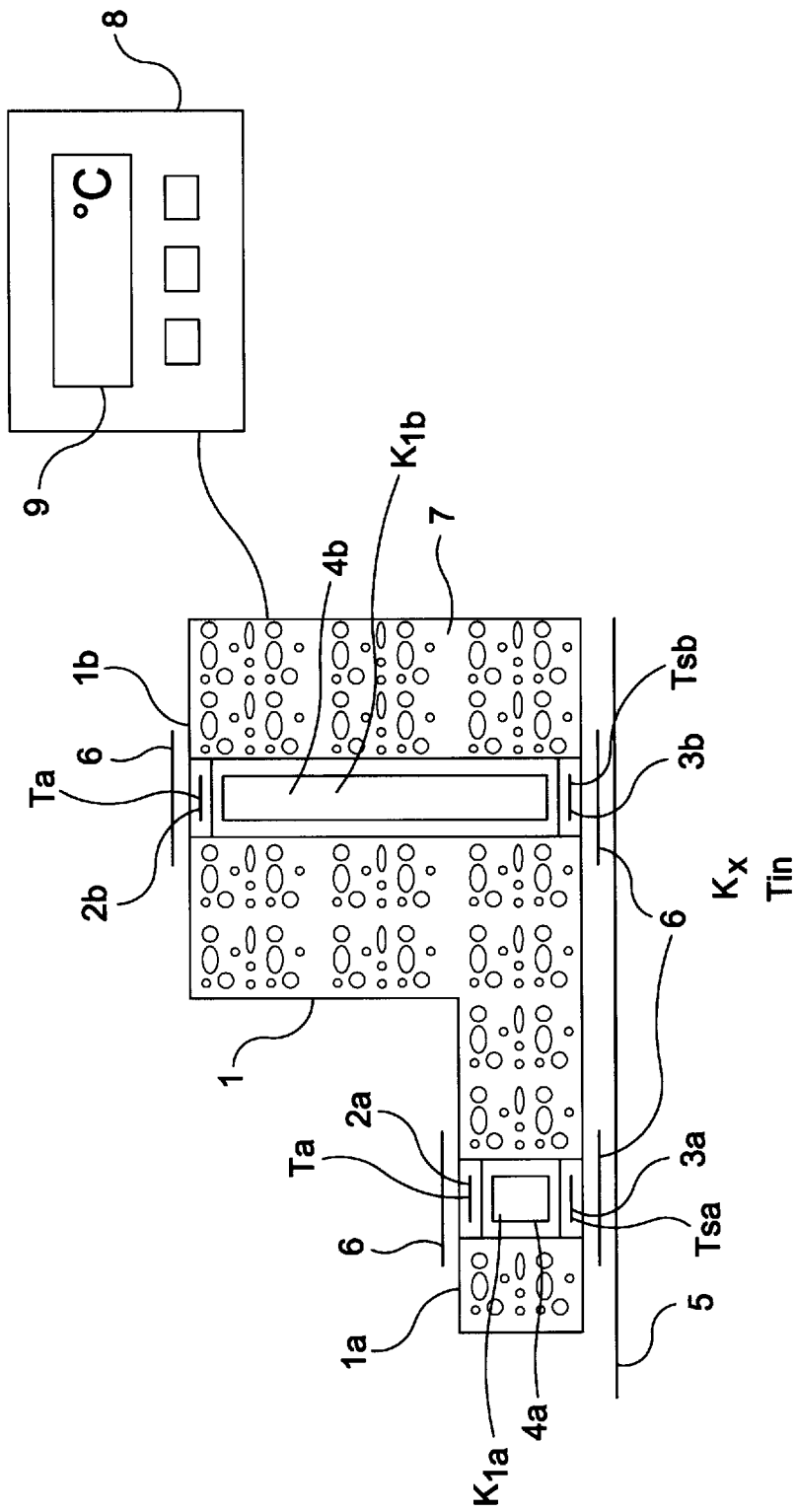

METHOD AND APPARATUS FOR DETERMINING INTERNAL TEMPERATURE AND COEFFICIENT OF INTERNAL THERMAL CONDUCTIVITY IN A STUCTURE

BACKGROUND OF THE INVENTION

1. Field of the Invention

The present invention relates to a method and an apparatus for determining the internal temperature of an object or body, said method comprising measuring heat flux from the surface of an object through a structure which is positioned against it and whose thermal conductivity is known.

2. Description of the Prior Art

Known solutions are implemented, for example, by thermometers measuring the temperature of a human being from the surface of the skin or by thermometers measuring the temperature of the contents of a process container from the surface of the container.

Heat flux through the surface layer of any object depends not only on the difference between the temperature of the object and the ambient temperature but also on the thermal conductivity of the object, the thermal conductivity being a characteristic of the material of which the object is made. The colour of the object has an effect on the temperature of the object: the darker the surface, the better it emits heat to the environment.

In measuring the thermal conductivity of the surface layer of living tissue, such as the human body, it has been found that thermal conductivity is clearly dependent on dermal circulation, i.e. on the coefficient of internal thermal conductivity. The basic level consists of the thermal conductivity of proteins and lipides, which is of the order of 1.8 mW/cm*K. When dermal circulation is stimulated, the water content of the tissue increases. Thus, when the circulation is at its most stimulated, the thermal conductivity of water, 6 mW/cm*K, can be added to the basic level of thermal conductivity. The range of thermal conductivity is thus from 1.8 to 7.8 mW/cm*K.

To develop a method for measuring the internal temperature of an object is a difficult task in many respects. The practical implementation requires solving of many problems, such as the effect of thermal losses, the calculation or measurement of internal temperature, calibration, etc. Determining the thermal conductivity of skin, for instance, is an extremely difficult task, and it is impossible unless calibration and approximation are performed for each measurement. Such a determination method is not suitable for rapid measurements in which the aim is to obtain relatively accurate results with a thermometer that is easy to use.

OBJECTS AND SUMMARY OF THE INVENTION

The object of the present invention is to provide a method and apparatus for determining the internal temperature in a structure simply and rapidly, directly from the surface of any object or living tissue. To achieve this, the method of the invention is characterized by measuring the surface temperature and ambient temperature of said object or body on both sides of two structures whose thermal conductance are known, eliminating the unknown thermal conductance of said object or body from the solutions by combining the doubled solutions and determining the internal temperature of said object or body on the basis of the combined solution.

The apparatus according to the invention for determining the internal temperature is based on a heat flux sensor to be positioned against the surface of an object or body for measuring heat flux from the surface of said object through the sensor. The apparatus according to the invention is characterized in that said apparatus comprises doubled sensors each of which comprises two thermosensitive elements positioned substantially opposite to each other, and a structure which is provided between them and whose thermal conductivity is known and by which the surface temperature and ambient temperature of said object or body can be measured, and a calculation unit by which the function of the heat flux in relation to the internal temperature of the object or body can be solved on the basis of the measured temperature values, and by which the doubled solutions can be combined to determine the internal temperature of said object or body on the basis of the combined solution.

The method and apparatus according to the invention for measuring the coefficient of internal thermal conductivity of an object of body and their preferred embodiments are characterized by what is disclosed in the appended claims.

BRIEF DESCRIPTION OF THE DRAWINGS

In the following, the invention will be described in greater detail with reference to the accompanying drawings, in which FIG. 3 illustrates an apparatus of the invention with its sensor structures.

DETAILED DESCRIPTION OF THE PREFERRED EMBODIMENTS

The invention allows the internal temperature of any object to be monitored by a measurement carried out on the surface of the object without the internal structure and thermal conductivity of the object being accurately known. The theoretical background of this discovery will be described briefly in the following.

Figure 1:
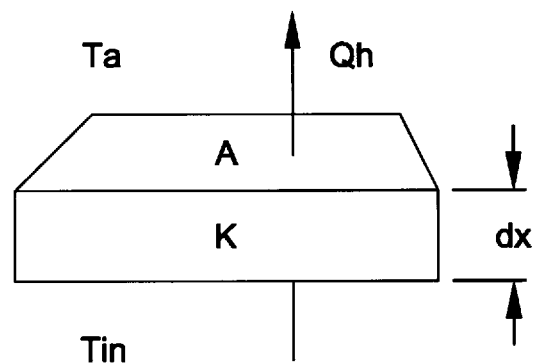
FIG. 1 illustrates the definition of thermal conductivity.

The thermal conductivity of a substance is defined by the formula $$K = \frac{Qh dx}{A dt dT} \qquad (1)$$

where Qh=heat flux through the substance, dx=thickness of the layer of substance, A=area of the object, dt=time, and dT=temperature difference between the surfaces of the substance/object, cf. FIG. 1.

In the following, two objects whose thermal conductivities are known are superimposed on an underlying surface whose temperature Tin is unknown. The structure is as shown in FIG. 2.

On the basis of the definition of the thermal conductivity of a substance it is possible to write a formula for heat flux through a certain area per a unit of time:

$$\frac{Qh}{A dt} = K \frac{dT}{dx} \qquad (2)$$

Figure 2:
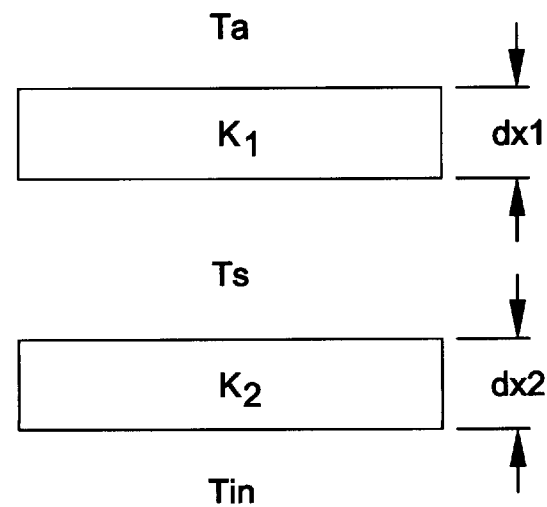
FIG. 2 illustrates the heat flux model utilized in the invention.

If it is assumed that the same heat flux runs perpendicularly through both objects, and if the temperature of the area between the objects is denoted by Ts, the coefficients of thermal conductivity of the objects are denoted by $K_1$ and $K_2$, and correspondingly their substance thicknesses by dx1 and dx2, the structure of FIG. 2 can thus be expressed as $$\frac{Qh}{Adt} = \frac{K_1}{dx1}(Ts-Ta) = \frac{K_2}{dx2}(Tin-Ts) \quad (3)$$

Further, if the coefficients are written as $$\frac{K_i}{dxi} = K'_i,$$

the following formula is obtained:

$$K'_1(Ts-Ta) = K'_2(Tin-Ts), \quad (4)$$

from which it is further possible to deduce the solution formula $$Tin = \frac{K'_2}{K'_1}(Ts-Ta) + Ts \quad (5)$$

Thus, if the coefficients of thermal conductivity of the insulating/conducting layers are known, the internal temperature of the object can be determined by measuring both the surface temperature and the ambient temperature of the object by means of the structure described above. A number of known heat flux measuring devices are based on this discovery, cf. e.g. U.S. Pat. Nos. 4,245,500, 4,541,728 and 4,553,852.

As it is usually difficult to accurately determine the thermal conductivity of another layer, i.e. an object or particularly a living tissue such as skin, the measurement is doubled in the invention, which gives the following pair of equations in accordance with Formula (4):

$$K_x(Tin-Tsa) = K_{1a}(Tsa-Ta) \quad (6)$$

$$K_x(Tin-Tsb) = K_{1b}(Tsb-Ta)$$

wherein $K_x$ is the unknown coefficient of thermal conductivity of the internal layer (corresponds to K2 in FIG. 2), e.g. skin; $K_{1a}$ and $K_{1b}$ are the coefficients of thermal conductivity of the two outer layers (correspond to $K_1$ in FIG. 2 and to 4a and 4b respectively in FIG. 3); and Tsa and Tsb are the corresponding temperatures of the surfaces between the layers (correspond to Ts in FIG. 2 and to temperatures measured by 3a and 3b, respectively, in FIG. 6).

If the two equations (6) are divided by each other, the following formula is obtained as a solution to the internal temperature Tin:

$$Tin = \frac{K_{1a}(Tsa-Ta)Tsb - K_{1b}(Tsb-Ta)Tsa}{K_{1a}(Tsa-Ta) - K_{1b}(Tsb-Ta)} \quad (7)$$

According to Formula (7), the value of Tin is no longer dependent on the unknown thermal conductivity $K_x$.

Formula (7) can further be reduced by writing $K = K_{1a}/K_{1b}$ in the form $$Tin = \frac{K(Tsa-Ta)Tsb - (Tsb-Ta)Tsa}{K(Tsa-Ta) - (Tsb-Ta)} \quad (8)$$

It is thus not necessary to know coefficients $K_{1a}$ and $K_{1b}$ accurately; instead, it is enough if the ratio between them is known. This can be easily arranged, for example, by making one of the insulating/conducting layers suitably thicker than the other one.

The formula proved above can be applied, for instance, for determining the internal temperature of a human body directly from the surface of the skin.

From the pair of equations (6), it is further possible to obtain the following expression for determining the coefficient of internal thermal conductivity $K_x$ of an object:

$$Kx = K_{1a} * \frac{Tsa-Ta}{Tsb-Ta} - K_{1b} \quad (9)$$

To determine the value of $K_x$ according to Formula (9), it is not necessary to know the internal temperature Tin of the structure. The formula can be applied, for example, for measuring the degree of dermal circulation of a human being or for monitoring changes in the structure of the wall of a process container.

The structure of the apparatus of the invention is shown in FIG. 3. The apparatus is based on a heat flux sensor 1 which is placed against the surface 5 of an object or body for measuring the heat flux from the surface of the object through the sensor. The apparatus of the invention comprises doubled sensors 1a and 1b, each of which consists of two thermosensitive elements 2a, 3a, or 2b, 3b respectively, positioned substantially opposite to each other, and a structure 4a or 4b whose thermal conductivity is known. The sensors measure the surface temperature of an object or body by means of thermosensitive elements, such as NTC thermistors 3a, 3b, and the ambient temperature by corresponding elements 2a, 2b. The NTC thermistors are preferably covered on the outside with a metal coating, such as copper plates 6, to enhance temperature conduction and to eliminate the effect of irrelevant variables, such as heat radiation which is dependent on the colours of the surfaces 5 and 6.

The structures 4a and 4b provided between the opposite thermosensitive elements 2a, 3a and 2b, 3b of the doubled sensors have preferably different thermal conductances. This is most easily achieved by the use of structures that are made of the same material but are of a different size. Such a case is illustrated in FIG. 3, where these structures consist of PTFE rods of different length. The structures 4a and 4b can also be made of different materials; the essential feature is that there are two independent series Ts, Ta (FIG. 2) of measurement results for each measurement.

According to a preferred embodiment of the invention, the doubled sensor construction 1 is an integral construction, and the sensors are thermally insulated from each other by an insulator, such as PS cellular plastic 7. In practice, there is a transverse heat flux in the sensor construction between the two sensors, as a result of which an offset component appears in Formula (7). The effect of the offset component can, however, be compensated for in advance.

The apparatus of the invention further comprises a calculation unit 8, by which the function of the heat flux in relation to the internal temperature of the object or body is determined on the basis of the measured temperature values (Formula 6). Thereafter the doubled solutions are combined in accordance with Formula 7 for determining the internal temperature of the object or body and for displaying it on the display 9 of the calculation unit.

The calculation unit 8 also stores the thermal conductivities $K_{1a}$ and $K_{1b}$ of the sensors 1a and 1b needed for the solutions of Formulae 6 and 7, or their ratio, and the above-mentioned offset component. In addition, the calculation unit is calibrated and adjusted so as to be ready for use, and it is optionally provided with a calibration function, by which the accuracy of the apparatus can be checked and set. It is obvious to one skilled in the art to describe the functions of a modern so-called ASIC circuit and to order them from a supplier with the necessary software for these kinds of devices performing relatively simple calculation and display functions.

The apparatus of the invention is preferably completely integrated, for example, in a case resembling a wrist watch;

the NTC thermistors 3a and 3b are thus located under the metal bottom shell of the device, and are thus continuously in contact with the skin of the person wearing the device. The temperature of the person can be read directly from the display, e.g. by pushing a button.

It will be obvious to one skilled in the art that the embodiments of the invention are not restricted to the examples described above, but that they may be modified within the scope of the appended claims.

It is claimed:

1. An apparatus for determining the internal temperature of one of an object and a body, said one of an object and a body having a surface, said apparatus comprising:
   a heat flux sensor, said heat flux sensor in turn comprising:
      first and second structures with at least a known ratio of thermal conductance, each of said structures having a first side and a second side opposite to said first side, said first side of said first structure and said first side of said second structure being positioned against said surface, said second side of said first structure and said second side of said second structure being in thermal communication with ambient temperature; and
      four thermosensitive elements positioned in substantially opposed pairs at said first and second sides of said first structure and said first and second sides of said second structure respectively, said four thermosensitive elements measuring:
         a surface temperature at said first side of said first structure and at said first side of said second structure; and
         a temperature of said second side of said first structure and of said second side of said second structure which are in thermal communication with said ambient temperature; and
   a calculation unit which calculates said internal temperature of said one of an object and a body via a doubled solution on the basis of:
      said surface temperature at said first side of said first structure;
      said surface temperature at said first side of said second structure;
      said temperatures of said second side of said first structure and said second side of said second structure; and
      said at least a known ratio of thermal conductance;
   wherein said doubled solution combines individual temperature solutions for each of said first and second structures.

2. An apparatus according to claim 1, wherein the first and second structures have different thermal conductances.

3. An apparatus according to claim 2, wherein the thermosensitive elements are NTC thermistors.

4. An apparatus according to claim 2, wherein the first and second structures are thermally insulated from each other.

5. An apparatus according to claim 1, wherein the thermosensitive elements are NTC thermistors.

6. An apparatus according to claim 5, wherein the outer surfaces of the NTC thermistors are covered with metal layers.

7. An apparatus according to claim 6, wherein the first and second structures are thermally insulated from each other.

8. The apparatus of claim 6, wherein said metal layers are copper plates.

9. An apparatus according to claim 5, wherein the first and second structures are thermally insulated from each other.

10. An apparatus according to claim 1, wherein the first and second structures are thermally insulated from each other.

11. A method for determining the internal temperature of one of an object and a body, said one of an object and a body having a surface, said method comprising the steps of:
   (a) providing a heat flux sensor having first and second structures with at least a known ratio of thermal conductance, each of said structures having a first side and a second side opposite to said first side;
   (b) positioning said sensor against said surface with said first side of said first structure and said first side of said second structure against said surface and said second side of said first structure and said second side of said second structure in thermal communication with ambient temperature;
   (c) measuring a surface temperature at said first side of said first structure and at said first side of said second structure;
   (d) measuring a temperature of said second side of said first structure and said second side of said second structure which are in thermal communication with said ambient temperature; and
   (e) determining said internal temperature of said one of an object and a body via a doubled solution on the basis of:
      said surface temperature at said first side of said first structure;
      said surface temperature at said first side of said second structure;
      said temperatures of said second side of said first structure and said second side of said second structure; and
      said at least a known ratio of thermal conductance;
   wherein said doubled solution combines individual temperature solutions for each of said first and second structures and eliminates an unknown thermal conductance of said one of an object and a body via said combination of said individual solutions.

12. The method of claim 11, wherein said providing step (a) includes providing said heat flux sensor with said first and second structures each having a different thermal conductance.

* * * * *

UNITED STATES PATENT AND TRADEMARK OFFICE
CERTIFICATE OF CORRECTION

PATENT NO. : 5,816,706
DATED : October 6, 1998
INVENTOR(S) : Heikkilä

It is certified that error appears in the above-identified patent and that said Letters Patent is hereby corrected as shown below:

On Cover Page, Title, reads "IN A STUCTURE" this should read --IN A STRUCTURE--

In Columm 1, Title, reads "IN A STUCTURE" this should read --IN A STRUCTURE--

In Column 1, Line 61, reads "conductance" this should read --conductances--

Signed and Sealed this

Ninth Day of February, 1999

Attest:

*Attesting Officer*

*Acting Commissioner of Patents and Trademarks*